(12) United States Patent
Edelman et al.

(10) Patent No.: US 7,191,798 B2
(45) Date of Patent: Mar. 20, 2007

(54) FLUID CIRCUIT CONNECTOR SYSTEM

(75) Inventors: Howard Edelman, San Francisco, CA (US); Howard R. Davidson, Palo Alto, CA (US)

(73) Assignee: Vital Wear, Inc., South San Francisco, CA (US)

( * ) Notice: Subject to any disclaimer, the term of this patent is extended or adjusted under 35 U.S.C. 154(b) by 0 days.

(21) Appl. No.: 10/326,714

(22) Filed: Dec. 19, 2002

(65) Prior Publication Data

US 2006/0260699 A1    Nov. 23, 2006

(51) Int. Cl.
*F16L 37/28* (2006.01)
(52) U.S. Cl. .............. 137/614.04; 137/595; 251/149.6
(58) Field of Classification Search ........... 137/614.04, 137/614.03, 614.05, 595; 251/149.6, 149.1; 285/308, 313
See application file for complete search history.

(56) References Cited

U.S. PATENT DOCUMENTS

| RE8,337 | E | 7/1878 | Gardner et al. |
|---|---|---|---|
| 430,721 | A | 6/1890 | Winkler |
| 2,322,449 | A | 6/1943 | Johnson et al. |
| 2,504,569 | A | 4/1950 | Murphy et al. |
| 2,518,299 | A | 8/1950 | Fernandez |
| 2,666,656 | A | 1/1954 | Bruning |
| 2,896,977 | A | 7/1959 | Hansen |
| 3,140,365 | A | 7/1964 | Voland |
| 3,191,972 | A * | 6/1965 | Collar |
| 3,283,780 | A | 11/1966 | Sutton |
| 3,284,842 | A | 11/1966 | Jennings, Jr. |
| 3,460,801 | A | 8/1969 | Norton |
| 3,586,048 | A | 6/1971 | Arnold |
| 3,788,348 | A | 1/1974 | Johnson |
| 3,916,929 | A | 11/1975 | Brown |
| 4,273,290 | A | 6/1981 | Quinn |
| 4,733,692 | A | 3/1988 | Kotake et al. |
| 4,989,790 | A | 2/1991 | Martin et al. |
| 5,013,013 | A | 5/1991 | Spedding |
| 5,234,166 | A | 8/1993 | Foster et al. |
| 5,316,041 | A * | 5/1994 | Ramacier, Jr. et al. .. 137/614.04 |
| 5,368,234 | A | 11/1994 | Foster et al. |
| 5,439,473 | A | 8/1995 | Jorgensen |
| 5,499,766 | A | 3/1996 | Foster et al. |

(Continued)

FOREIGN PATENT DOCUMENTS

IT    246899    4/2002

(Continued)

*Primary Examiner*—Kevin Lee
(74) *Attorney, Agent, or Firm*—Kang Lim

(57) ABSTRACT

A fluid circuit connector system includes a quick-release connector for connecting a set of tubes to an object. The quick-release connector includes a release button, a lock arm, a lock tab and a cavity configured to receive the tubes and a set of coupler housings. The connector system includes an object fitting having lock recess may be configured to receive the lock tab. The object fitting includes a cavity. The system further includes a set of male coupler housings each including a first unitary valve and a set of female coupler housings each including a second unitary valve. Each female housing is configured to receive and engage one of the male coupler housings. The system includes a set of seals configured to seal each male coupler housing and each female coupler housing when the quick-release connector is connected to the object fitting.

20 Claims, 5 Drawing Sheets

U.S. PATENT DOCUMENTS

| | | |
|---|---|---|
| 5,668,565 A | 9/1997 | Robinson |
| RE35,744 E | 3/1998 | Foster et al. |
| 5,755,733 A | 5/1998 | Morita |
| 6,050,297 A * | 4/2000 | Ostrowski et al. ..... 137/614.04 |
| 6,270,055 B1 | 8/2001 | Szeteli et al. |
| 6,299,626 B1 | 10/2001 | Viranyi |
| 6,827,728 B2 * | 12/2004 | Ellingboe et al. ........... 137/594 |

FOREIGN PATENT DOCUMENTS

| | | |
|---|---|---|
| SU | 577-350 | 10/1977 |

* cited by examiner

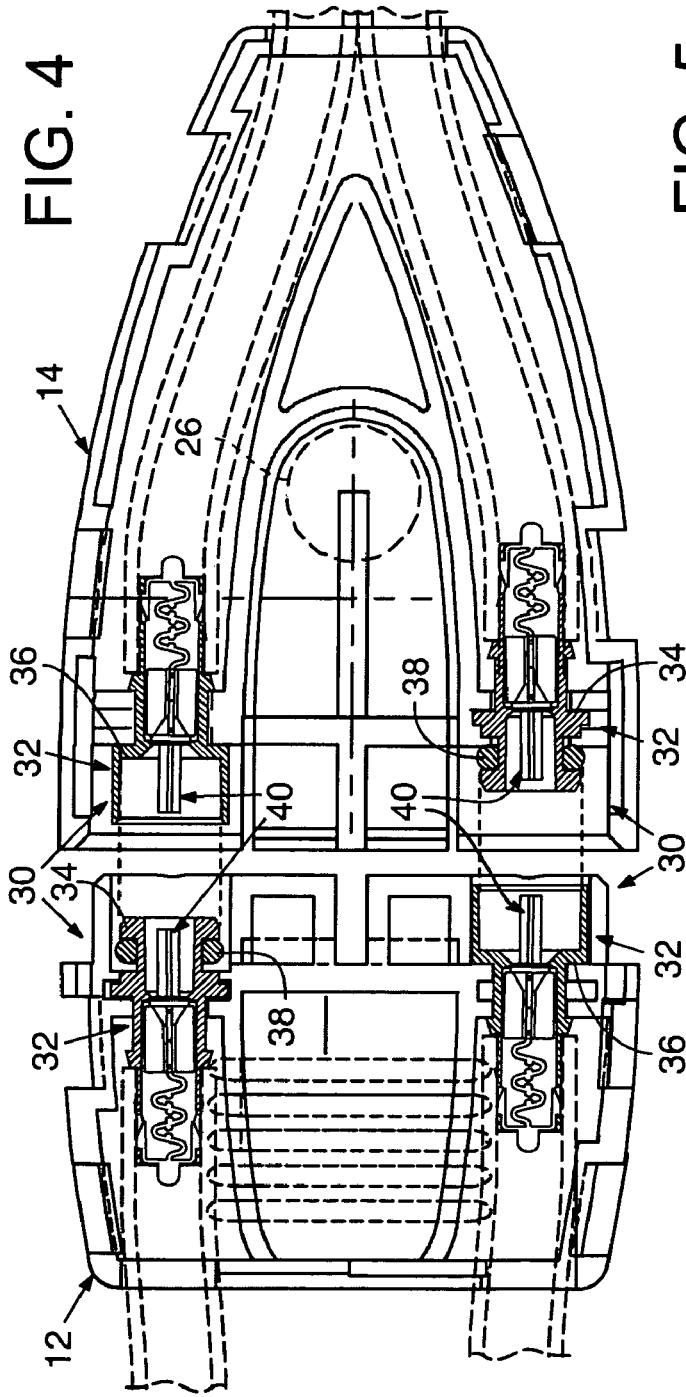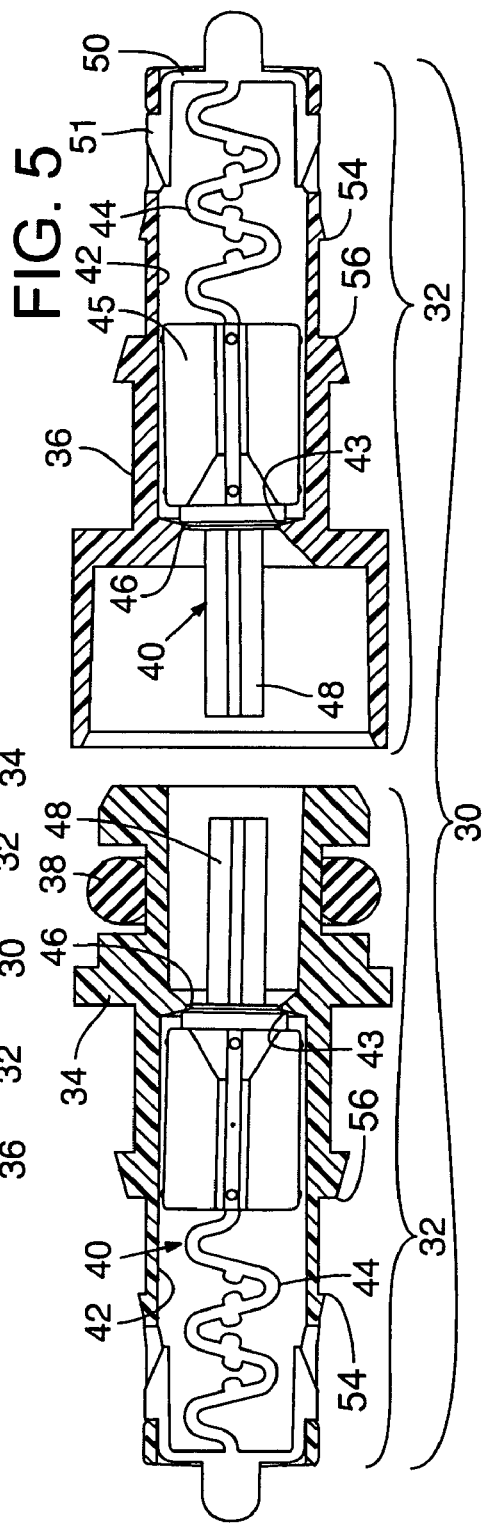

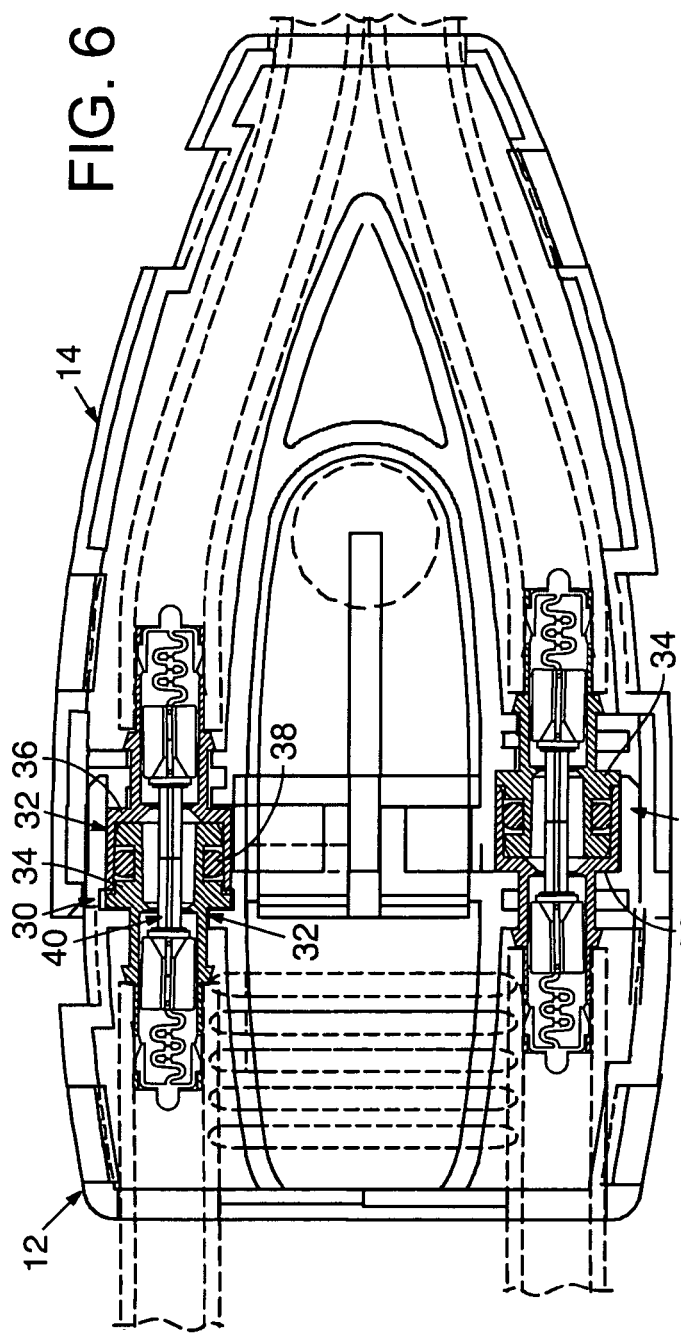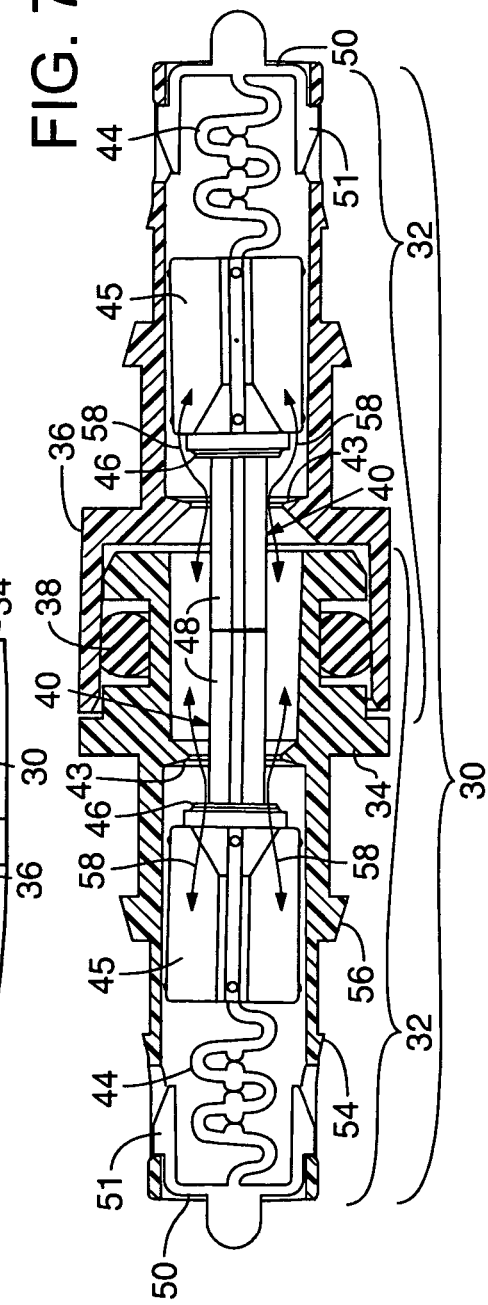

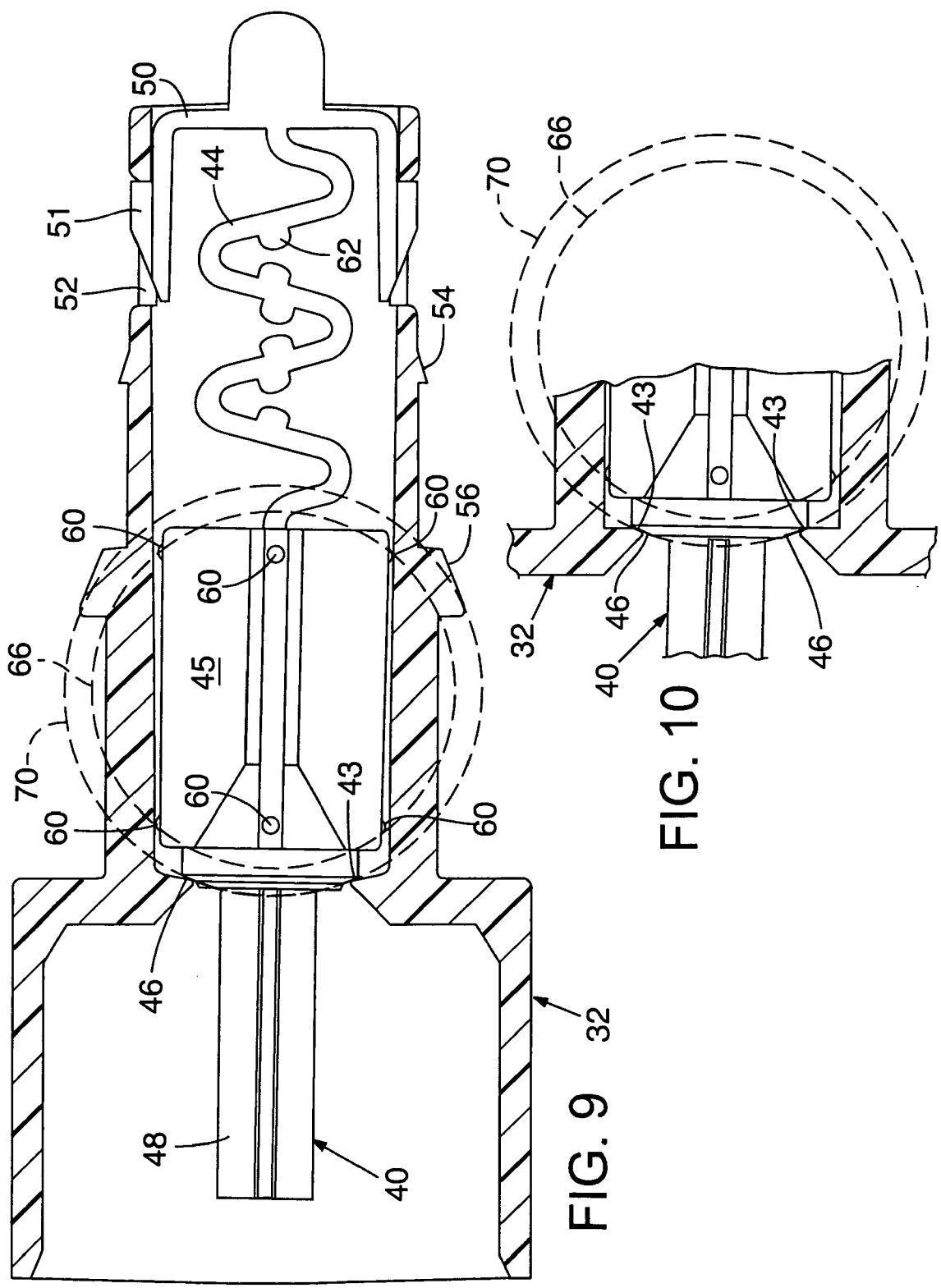

FLUID CIRCUIT CONNECTOR SYSTEM

FIELD OF THE INVENTION

The present invention relates generally to fluid circuit connector systems. More specifically, the invention concerns quick-release connectors having couplers with single part unitary valves for controlling fluid leakage.

BACKGROUND OF THE INVENTION

Fluid circuits are useful in a variety of contexts, particularly providing hot and/or cold therapeutic treatments to sore body parts. The potential effectiveness of a hot or cold treatment increases with the level of temperature control. Precise temperature control can be achieved through a carefully controlled fluid circuit. Fluids have a high rate of heat transfer and the precise temperature may be quickly changed and easily maintained. Examples of devices for delivering hot or cold fluids for therapeutic purposes include United State Patent Publication No. 2001/0039439 A1 to Elkins and U.S. patent application Ser. No. 10/267,247 filed on Oct. 8, 2002, and entitled Contrast Therapy System and Method, both of which are incorporated herein by reference.

Therapy devices configured to deliver hot and cold treatments may employ one or more reservoirs of fluid. Often these devices include one hot fluid reservoir and one cold fluid reservoir configured to connect via a fluid circuit to a therapy pad or wrap. The therapy pad or wrap may be configured to fit a specific part of the body. For example, wraps are often designed to apply therapy to a limb, such as an arm or a leg, and pads are often designed to apply therapy to the torso, particularly the back or shoulders.

It may be desirable to easily interchange between wraps or pads of varying capacity and size. To achieve interchangeability a fluid circuit connector system may be desirable.

SUMMARY OF THE INVENTION

A fluid circuit connector system includes a quick-release connector for connecting a set of tubes to an object. The quick-release connector includes a release button, a latch arm, a latch tab and a cavity configured to receive the tubes and a set of coupler housings. The connector system includes an object fitting having latch recess that may be configured to receive the latch tab. The object fitting includes a cavity. The system further includes a set of male coupler housings each including a first unitary valve and a set of female coupler housings each including a second unitary valve. Each female housing is configured to receive and engage one of the male coupler housings. The system includes a set of seals configured to seal each male coupler housing and each female coupler housing when the quick-release connector is connected to the object fitting.

BRIEF DESCRIPTION OF THE DRAWINGS

FIG. 4 is a partially sectioned top view of an embodiment of a quick-release connector of the present invention showing a disconnected configuration.

FIG. 5 is a partially sectioned side view of a fluid coupler according to an embodiment of the present invention, shown in a disconnected and closed configuration.

FIG. 6 is a partially sectioned top view of the quick-release connector of FIG. 4, shown in a connected configuration.

FIG. 7 is a partially sectioned side view of the fluid coupler of FIG. 5, shown in a connected and open configuration.

FIG. 9 is a partially sectioned side view of a fluid coupler housing and a unitary valve illustrating concentric spherical radii, which define the relative position of a valve seat and a set of valve guides.

FIG. 10 is an enlarged view of FIG. 9, showing a partially sectioned a cut away View of the valve seat and housing seat of and embodiment of the present invention.

DETAILED DESCRIPTION OF THE INVENTION

Figure 1:
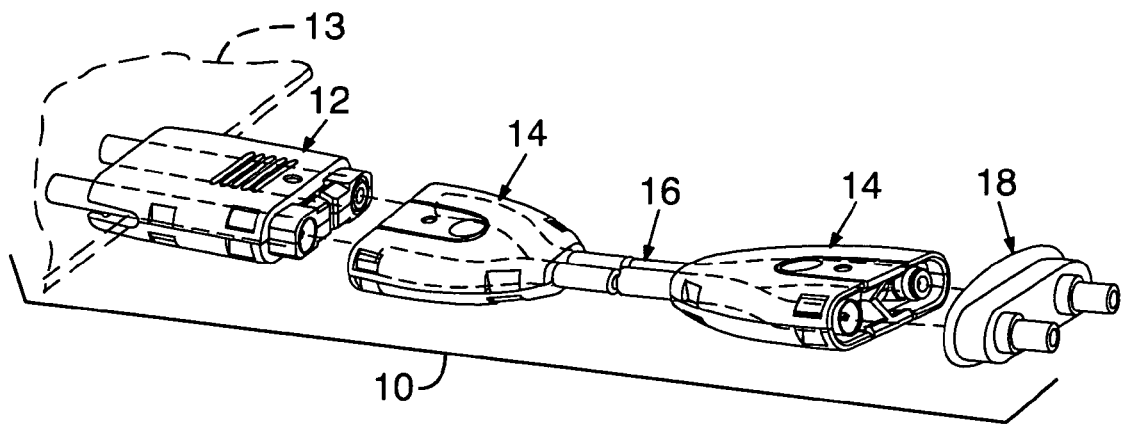
FIG. 1 is a perspective view of an embodiment of a fluid circuit connector system according to the present invention.

The present invention relates to a fluid circuit connection system, an embodiment of which is shown in FIG. 1, indicated generally at 10. Although useful for a variety of fluid circuit systems, the illustrated embodiment is shown in the context of a contrast therapy wrap. Fluid circuit connection system 10 includes an object fitting 12, as shown the object fitting is connected to a contrast therapy applicator 13, such as a pad or wrap. Contrast therapy applicator 13 may be any of a variety of contrast therapy applicators including arm wraps, leg wraps, waist wraps, shoulder wraps, and pads for applying therapy to various sore body parts. Object fitting 12 may be configured to receive a quick-release connector 14 attached to one end of a set of tubes 16. At the other end of tube set 16 is another quick-release connector 14 configured to connect to a source fitting 18. Source fitting 18 connects the fluid circuit to a source of hot and cold fluid for circulation.

It will be understood that in the illustrated embodiment both quick-release connectors 14 may be used to attach to either object fitting 12 or source fitting 18. Other embodiments of the present invention may have quick-release connectors 14 that may be fitting specific. For example, a quick-release connector configured to attach to object fitting 12 may not connect to source fitting 18 and vice versa. This may be desirable for enabling the use of a contrast therapy fluid supply with a variety of therapy wraps and pads that may have different types and or sizes of object fittings.

Figure 2:
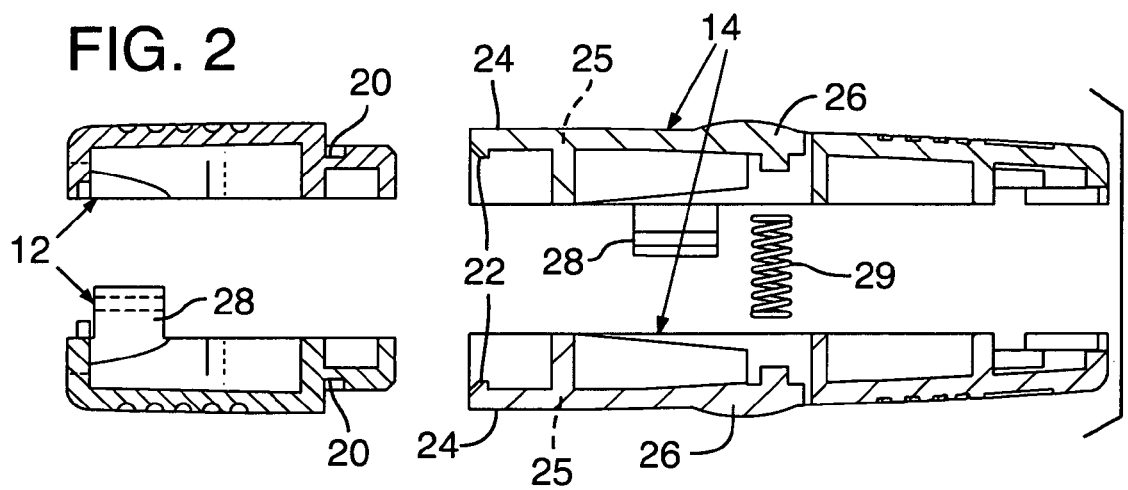
FIG. 2 is an exploded and sectioned side view of an embodiment of a quick-release connector for use with the fluid circuit connector system of FIG. 1.
Figure 3:
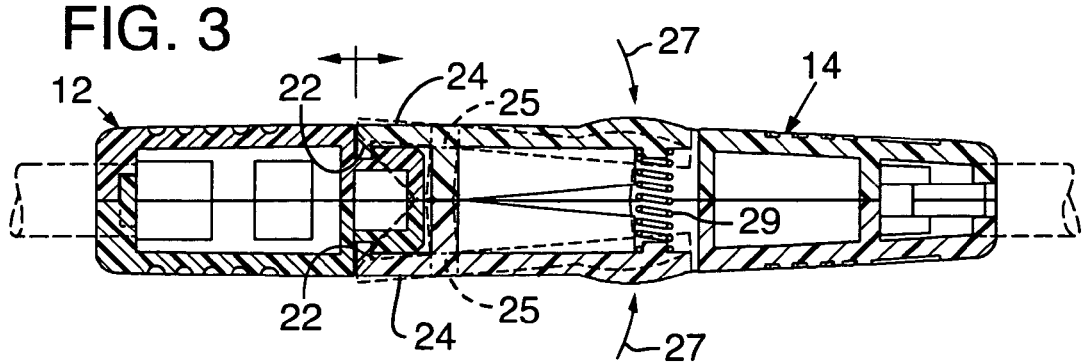
FIG. 3 is a sectional side view of the quick-release connector of FIG. 2, shown in a connected configuration.

FIGS. 2 and 3 show the latch operation of object fitting 12 and quick-release connector 14. Object fitting 12 includes latch recesses 20 configured to receive latch tabs 22 from quick-release connector 14. Latch tabs 22 may be positioned at the ends of latch arms 24 of quick-release connector 14. Latch arms 24 may be attached to connector 14 at a thinned rotational flex point 25. Latch release buttons 26 may be attached to quick-release connector 14 on an opposed side of flex point 25 from latch arms 24. Latch buttons 26 are biased outward by a biasing member 29. The outward bias of latch buttons 26 causes a slight inward bias to latch arms 24 on the opposite side of flex point 25.

Quick-release connector 14 may be connected to object fitting 12 by depressing latch buttons 26 with a squeezing motion, as illustrated in FIG. 3, by arrows 27. Depressing latch buttons 26 causes latch arms 24 to spread out, as illustrated in dashed lines in FIG. 3. With latch buttons 26 depressed, quick-release connector 14 may be pushed into engagement with object fitting 12. Once quick latch 14 is pushed into engagement, latch buttons 26 may be released causing spring 29 to urge latch arms 24 to close together and latch tabs 22 to engage latch recesses 20, thus securing connector 14 to fitting 12.

As shown in FIG. 2, object fitting 12 and quick latch connector 14 may be made of two halves that are held together with snap fittings 28. Pressing each half together around the tubes and couplers carrying fluid to the object or from the object completes the fitting and connector. Other constructions for object fitting 12 and quick-release connector 14 may also be used.

Releasing quick-release connector 14 may be accomplished by simply reversing the above process. First, depress latch buttons 26 spreading latch arms 24 and causing latch tabs 22 to release from latch recesses 20. Second, pull quick-release connector 14 from object fitting 12.

Source fitting 18 similarly includes latch recesses configured to receive latch tabs 22 of quick lock connector 14. Therefore, quick-release connector 14, which is attached to the other end of tube set 16, may be connected to and released from source fitting 18 in the same manner as described with regard to object fitting 12. It will be understood that both quick-release connectors 14 are constructed in the same manner and may be used to attach to either object fitting 12 or source fitting 18.

FIG. 4 shows object fitting 12 and quick-release connector 14 in a disconnected configuration. Object fitting 12 and quick-release connector 14 may each include two halves of a fluid coupler 30. Fluid coupler 30 is a device configured to permit the ends of two tubes to couple in fluid communication with one another and to seal the ends of the two tubes upon decoupling.

Each fluid coupler includes a pair of coupler housings 32. Coupler housings 32 may include two types. A male coupler housing 34 may be configured for insertion into a female housing 36. Object fitting 12 may include one of each type of housing, as shown in FIG. 4, or may include two of the same types of coupler housings. It will be understood that, if object fitting 12 has one of each type of coupler housing, then in a corresponding location quick-release connector 14 must have the complementary coupler housing type. For example, as shown in FIG. 4, object fitting 12 includes male coupler housing 34 in a top location and female coupler housing 36 in a bottom location, therefore quick-release connector 14 should have female coupler housing 36 in a top location and male coupler housing 34 in a bottom location.

Fluid coupler 30 may include a seal 38 to prevent fluid from escaping between male coupler housing 34 and female coupler housing 36. Seal 38 may be an O-ring type seal that is configured to sit in place in a groove cut in male housing 36. It will be understood that seal 38 may include other suitable sealing gaskets or mechanisms and may be configured to sit in place in either the male of female coupler housing.

In operation, quick-release connector 14 and object fitting 12, or source fitting 18, will fully latch prior to male coupler housing 34 and female coupler housing 36 bottoming out against one another. This ensures that the quick-lock connector engages properly and prevents the coupler housings from interfering with a proper latch between quick-lock connector 14 and one of the fittings.

Each coupler housing 32 includes a valve assembly. It follows that each fluid coupler 30 then includes two valve assemblies. A valve assembly may be configured to open a fluid flow path between two tube ends. Tubes may be press fit over the ends of coupler housings 32 to enable fluid communication between the tubes and the fluid coupler.

FIG. 5 illustrates a decoupled fluid coupler 30. Fluid coupler 30 may include two main components, namely coupler housings 32 and unitary valve 40. The combination of portions of coupler housing 32 and unitary valve 40 may be referred to as a valve assembly. Unitary valve 40 cooperates with a housing seat 43 in housing 32 to seal off one section of housing 32 from another section. Housing seat 43 may be formed integral with coupler housing 32. Unitary valve 40 may be configured to fit within coupler housing 32. For example, coupler housing 32 may include an elongate bore 42 adapted to receive unitary valve 40 axially within elongate bore 42. Housing seat 43 may be positioned within elongate bore 42 of coupler housing 32.

Unitary valve 40 may include a biasing member 44 configured to bias the unitary valve into engagement with housing seat 43. Unitary valve 40 may include a stabilizer 45 formed integral with biasing member 44 and configured to aid in the alignment of valve assembly 40. A valve seat surface 46 may be formed integral with stabilizer 45 and biasing member 44 and configured to engage housing seat 43 to close unitary valve 40 and prevent leakage from the end of a tube connected therewith. Unitary valve 40 further includes a valve stem 48 formed integral with valve seat 46, stabilizer 45, and biasing member 44. Valve stem 48 may be configured to receive a force opposing biasing member 44 to open unitary valve 40, as will be explained in detail below.

Unitary valve 40 may include a retainer 50 configured to hold the unitary valve within fluid coupler housing 32. Retainer 50 may include retainer prongs 51. Fluid coupler housing 32 may include retainer detents 52 configured to receive retainer prongs 51 of retainer 50 and secure unitary valve 40 inside bore 42 of fluid coupler housing 32.

Coupler housings 32 may include a barb 54 positioned near one end of each coupler housing and configured to aid in retaining a press fit tube that has been pressed onto the coupler housing. Each housing may also include a flange 56 configured to limit the distance that a press fit tube may extend over coupler housing 32. A tube is fully press fit when the end of the tube abuts flange 56. In the depicted embodiment, the tube seals off retainer detents 52 preventing fluid from escaping from these openings. It will be understood that this sealing function may not occur if detents 52 do not open up to the outside of housing 32.

As depicted in FIG. 5, fluid coupler 30 is in a decoupled configuration. In the decoupled configuration valve seat 46 engages with housing seat 43 to block the flow of fluid out of the end of coupler housing 32. Biasing member 44 applies a biasing force to valve seat 46 through stabilizer 45 to press valve seat 46 into housing seat 43 and seal the valve. Stabilizer 45 along with valve guides 60 act to limit the misalignment of unitary valve 40 with respect to bore 42 of coupler housing 32. Valve stem 48 extends toward a coupling end of coupler housing 32 and is configured to cause the valve to open when valve stem 48 is engaged and pressed reward in the coupler housing by opposing valve stem 48.

FIG. 6 depicts object fitting 12 and quick-release connector 14 in a connected configuration. In the connected configuration each fluid coupler is coupled and configured to permit fluid to flow through the coupler. A detailed view of the fluid coupler, illustrated uncoupled in FIG. 5, is shown in a coupled configuration in FIG. 7. Flow arrows 58 illustrate the fluid flow path through the coupled fluid coupler 30.

In the coupled fluid coupler of FIG. 7, the coupling end of male housing 34 slides into the coupling end of female housing 36. Initially, as the two housings 34 and 36 slide together, seal 38, which may be an O-ring type seal or any other suitable sealing member, engages and seals the coupling ends of the two housing to prevent fluid leaks. As the two housings 34 and 36 slide further together valve stems 48 of each coupler housing 32 engage one another causing the two biasing members 44 to compress. Compressing biasing members 44 permits the rest of unitary valves 40 to slide away from the coupling ends of coupling housings 32. As unitary valve 40 slides away from the coupling end of coupling housing 32, valve seat 46 separates from housing seat 43 opening a path for fluid to flow through, as illustrated by flow arrows 58. It will be understood that seal 38 seals the two housings prior to either unitary valve opening.

Figure 8:
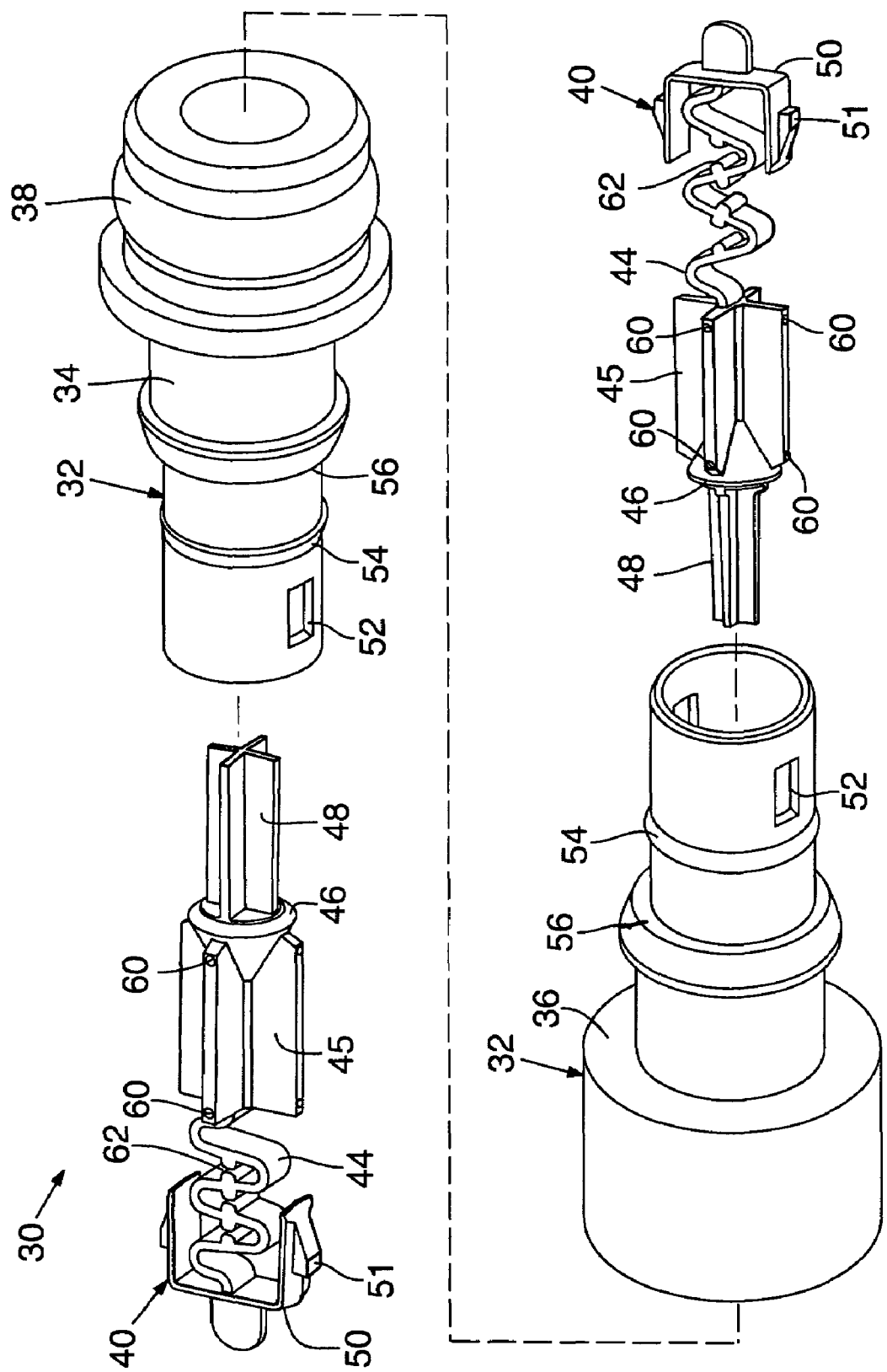
FIG. 8 is an exploded assembly view of the fluid coupler of FIGS. 5 and 7.

FIG. 8 illustrates the assembly of unitary valves 40, male coupler housing 34, and female coupler housing 36. Valve stem 48 includes an X-shaped cross section, which allows opposed valve stems to engage as intended with an increased amount of misalignment between the opposed valve stems while maintaining an adequate flow passage. While valve stem 48 is shown with an X-shaped cross section it will be understood that other embodiments may employ other shapes.

As noted above, stabilizer 45 includes a series of radial fins extending radially from a central region. Stabilizer 45 includes a plurality of valve guides 60 positioned on the ends of fins and configured to engage the interior wall of bore 42 in coupler housing 32. Engaging the interior wall of bore 42 in coupler housing 32 provides an alignment function for unitary valve 40. The geometry of stabilizer 45 may be configured to provide a stabilizing function to the unitary valve, while minimizing the interference with fluid flow when the valve assembly is open.

In the depicted embodiment biasing member 44 of unitary valve 40 is a ribbon spring. Each ribbon spring may include a set of compression limits 62. Compression limits 62 prevent either one of the ribbon springs in a coupler from being over compressed preventing the opposing valve from opening. For example, if one ribbon spring is less stiff than the opposing spring it will bottoms out on compression limits 62 first and the other spring will begin to compress as housings 34 and 36 are pressed further together. In this way, the other valve will fully unseat and open a flow path before male housing 34 is completely inserted into female housing 36. Other configurations for biasing member 44 may be used including a coil type spring, an elastic member, or other structure capable of biasing the unitary valve.

Unitary valve 40 may be inserted into bore 42 in a tube-attaching end 63 of coupler housing 32. When unitary valve 40 is fully inserted and the ribbon spring preloaded, retainer detents 52, positioned close to tube-attaching end 63, may be configured to receive retainer prong 51 extending from retainer 50. This configuration holds the unitary valve in place inside the coupler housing. This process applies to both the male coupler housing and the female coupler housing.

FIG. 9 illustrates the misalignment interaction between coupler housing 32 and valve guides 60. Semispherical valve guides 60 are positioned on stabilizer 45, such that those points of valve guides 60 where contact with bore 42 may occur all lie on a theoretical valve guide spherical surface 66. Valve seat 46 includes a spherical surface that lies in theoretical spherical surface 70 that is concentric with theoretical valve guide spherical surface 66. Valve assembly 40 may function properly with larger tolerances between bore 42 of coupler housing 32 and valve guides 60 because of the concentric configuration of the contact points of valve guides 60 and valve seat surface, which lies in theoretical spherical surface 70.

For example, a misalignment that causes two of the valve guides 60 to contact bore 42 of the coupler housing can occur simultaneously with the surface of valve seat 46 fully engaging housing seat 43, as illustrated in FIG. 10. That is to say, valve seat 46 will properly engage and prevent leakage even though unitary valve 40 is maximally misaligned, such misalignment being limited by one or more of valve guides 60 contacting the bore wall 42 of housing 32.

While the present invention has been particularly shown and described with reference to the foregoing preferred embodiments, those skilled in the art will understand that many variations may be made therein without departing from the spirit and scope of the invention as defined in the following claims. The description of the invention should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

We claim:

1. A valve assembly comprising:
   a unitary valve;
   a housing having an elongate bore configured to receive the unitary valve axially;
   wherein the unitary valve includes:
      a valve seat;
      a valve stem extending forward from the valve seat and formed integral therewith;
      a stabilizer extending rearward from the valve seat and formed integral therewith; and
      a biasing member extending rearward from the valve stabilizer and formed integral therewith.

2. The valve assembly of claim 1, wherein the valve seat includes a surface having a first spherical radius of curvature.

3. The valve assembly of claim 2, wherein the stabilizer includes a plurality of fins extending radially and having valve guides positioned on the edges thereof.

4. The valve assembly of claim 3, wherein the valve guides are positioned on the fins of the stabilizer such that the valve guides contact the elongate bore wall at an intersection of the elongate bore wall and a hypothetical second spherical surface, which is concentric with the first spherical radius.

5. The valve assembly of claim 4, wherein the valve seat will properly engage and prevent leakage even though the valve is maximally misaligned, such misalignment being limited by at least one valve guide contacting the elongate bore of the housing.

6. The valve assembly of claim 1, wherein the valve stem includes an X-shaped cross section.

7. The valve assembly of claim 1, wherein the biasing member includes a ribbon spring.

8. The valve assembly of claim 1, wherein the unitary valve further includes a retainer having a retainer prong.

9. A fluid coupler comprising:
   a male coupler housing including a first unitary valve;
   a female coupler housing including a second unitary valve and configured to receive the male coupler housing;
   a seal configured to be positioned between the male coupler housing and the female coupler housing when they are connected preventing fluid from leaking out from the connected fluid coupler;

wherein the first unitary valve and the second unitary valve each include:
- a valve seat;
- a valve stem extending forward from the valve seat and formed integral therewith;
- a stabilizer extending rearward from the valve seat and formed integral therewith; and
- a biasing member extending rearward from the valve stabilizer and formed integral therewith.

10. The fluid coupler of claim 9, wherein each unitary valve includes a retainer having a retainer prong formed integral with the unitary valve.

11. The fluid coupler of claim 10, wherein:
the male coupler housing includes a retainer detent for engaging the retainer prong of the first unitary valve; and
the female coupler housing includes a retainer detent for engaging the retainer prong of the second unitary valve.

12. The fluid coupler of claim 9, wherein each of the male coupler housing and the female coupler housing each include a barb for preventing a press fit tube from slipping off.

13. The fluid coupler of claim 9, wherein the fluid coupler is configured to be in one of a coupled position and an uncoupled position, wherein in the coupled position the unitary valves are open permitting fluid flow through the coupler and in the uncoupled position the unitary valves are closed preventing fluid leakage.

14. A fluid circuit connector system comprising:
a quick-release connector for connecting a set of tubes to an object, wherein the quick-release connector includes a release button, a lock arm, a lock tab and a cavity configured to receive the tubes and a set of coupler housings;
an object fitting having lock recess configured to receive the lock tab and a cavity;
a set of male coupler housings each including a first unitary valve and configured to fit within the cavity;
a set of female coupler housings each including a second unitary valve and configured to fit within the cavity, wherein each female coupler is configured to receive and engage one of the male coupler housings; and
a set of seals configured to be positioned between each male coupler housing and each female coupler housing when the quick-release connector is connected to the object fitting.

15. The fluid circuit connector system of claim 14, wherein the quick-release connector is formed from two halves that snap fit together.

16. The fluid circuit connector system of claim 14, wherein each male and female housing includes a bore for receiving a unitary valve and a housing seat.

17. The fluid circuit connector system of claim 14, wherein the first and second unitary valves each include:
- a valve seat;
- a valve stem extending forward from the valve seat and formed integral therewith;
- a stabilizer extending rearward from the valve seat and formed integral therewith; and
- a biasing member extending rearward from the valve stabilizer and formed integral therewith.

18. A contrast therapy system, comprising:
a therapy fluid source having a bulk head fitting;
a therapy wrap having an object fitting;
a fluid circuit tube set having a quick-release connector attached to each end thereof, wherein the quick-release connectors include fluid couplers and are configured to attached to the bulk head fitting and the object fitting;
wherein the fluid couplers include:
a male coupler housing including a first unitary valve;
a female coupler housing including a second unitary valve and configured to receive the male coupler housing; and
a seal configured to be positioned between the male coupler housing and the female coupler housing when they are connected preventing fluid from leaving out from the connected fluid coupler; and
wherein the first unitary valve and the second unitary valve each include:
- a valve seat;
- a valve stem extending forward from the valve seat and formed integral therewith;
- a stabilizer extending rearward from the valve seat and formed integral therewith; and
- a biasing member extending rearward from the valve stabilizer and formed integral therewith.

19. The contrast therapy system of claim 18, wherein each unitary valve includes a retainer having a retainer prong formed integral with the unitary valve.

20. The contrast therapy system of claim 19, wherein:
the male coupler housing includes a retainer detent for engaging the retainer prong of the first unitary valve; and
the female coupler housing includes a retainer detent for engaging the retainer prong of the second unitary valve.

* * * * *